(12) United States Patent
Levin

(10) Patent No.: US 6,194,160 B1
(45) Date of Patent: *Feb. 27, 2001

(54) SYSTEMS AND METHODS FOR RAPID BLOT SCREENING

(75) Inventor: Andrew E. Levin, Wellesley, MA (US)

(73) Assignee: Immunetics, Inc., Cambride, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/045,630

(22) Filed: Mar. 19, 1998

(51) Int. Cl.[7] .................................................. G01N 33/543
(52) U.S. Cl. .......................... 435/7.1; 422/56; 422/58; 422/101; 422/102; 435/287.1; 435/287.2; 435/287.7; 435/288.5; 436/518; 436/809
(58) Field of Search ............................ 422/56, 58, 101, 422/102; 435/7.1, 287.1, 287.2, 287.7, 288.5; 436/518, 809

(56) References Cited

U.S. PATENT DOCUMENTS

| | | | |
|---|---|---|---|
| 4,777,021 | * 10/1988 | Wertz et al. | 422/101 |
| 4,797,259 | * 1/1989 | Matkovich et al. | 422/101 |
| 4,834,946 | 5/1989 | Levin | 422/101 |
| 4,895,706 | * 1/1990 | Root et al. | 422/102 |
| 5,567,595 | 10/1996 | Kok | 435/7.92 |

FOREIGN PATENT DOCUMENTS

| | | |
|---|---|---|
| 0 720 020 | 7/1996 | (EP) . |
| WO 90/09455 | 8/1990 | (WO) . |
| WO 94/08716 | 4/1994 | (WO) . |
| WO 99/00655 | 1/1999 | (WO) . |
| WO 99/05528 | 2/1999 | (WO) . |

OTHER PUBLICATIONS

International Search Report.

* cited by examiner

Primary Examiner—Christopher L. Chin
(74) Attorney, Agent, or Firm—Foley, Hoag & Eliot LLP

(57) ABSTRACT

Systems and methods for processing membrane flow-through assays to provide more rapid testing. The systems include a plate for receiving a cartridge having a membrane which, for example, can be a membrane with antigens or antibodies fixed thereon. The agents can be pipetted onto the membrane and the systems can be activated to agitate the cartridge to evenly distribute the agents over the membrane, and a vacuum source can apply negative pressure to one side of the membrane to draw the agent therethrough.

19 Claims, 6 Drawing Sheets

SYSTEMS AND METHODS FOR RAPID BLOT SCREENING

FIELD OF THE INVENTION

The invention relates to medical instrumentation for in vitro diagnostics, and more particularly to medical instrumentation for more efficiently conducting accurate assay for the in vitro diagnosis of infectious diseases.

BACKGROUND OF THE INVENTION

The successful medical treatment of a disease depends, in part, on an accurate diagnosis. Traditionally, diagnosis is done by examining a patient's symptoms and comparing the identified symptoms against the list of known symptoms that are associated with each known disease. Given the range of known diseases this can be a difficult task, particularly for young children in distress who are less capable of describing their symptoms and less capable of confirming for the treating physician contact with significant environmental factors, such as exposure to certain plants, animals or insects.

To improve the accuracy of this process, scientists have developed new testing techniques that identify from a sample of the patient's blood, the existence of pathogens indicative of the disease. More specifically, patients infected with microbial pathogens develop an immune response characterized by the appearance in the patient's serum of antibodies specific to microbial antigens. Such antibodies can be detected in various ways, and their detection can serve as an indication of infection and the existence or likely development of a particular disease. Consequently, the medical community has adopted these tests as part of the process of diagnosing serious infectious diseases, such as HIV, hepatitis and Lyme disease. The standard test performed is the Enzyme-Linked Immunosorbent Assay (ELISA). The ELISA test provides an efficient way to test for the presence of antibodies of interest. However, ELISA can provide false or questionable test results up to 20% of the time, depending on the specific test. To overcome this drawback, doctors retest specimens with a more accurate membrane-based assay, such as the Western blot test.

The Western blot test involves preliminary electrophoretic separation of antigen components by molecular weight on polyacrylamide gels, followed by transfer of the separated antigen bands to a membrane. In the Western Blot method, antibody reactions to specific antigen bands can be detected and distinguished from antibody reactions with non-specific or cross-reactive bands, thereby significantly increasing the specificity of the immunoassays. The Western blot method has become the method of choice in confirming the presence of antibodies specific for a range of infections, including HIV, HTLV-1/2, Lyme Disease, and Cysticercosis.

However, the Western blot assay is cumbersome and labor intensive. In current practice, the Western blot method comprises a sequence of incubation and wash steps performed on a membrane bearing resolved antigen bands. Typically, the membrane is cut into narrow strips, each bearing the identical pattern of antigen bands. Strips are then processed in reagent solutions individually in narrow trays. In the first step, the strip is incubated with a blocking solution containing a non-specific protein. After washing off excess blocking solution with a wash buffer, the strip is incubated with antibody solution. Unbound antibody is then washed off with buffer and the strip is incubated in the detection reagent. Unbound detection reagent is washed off with buffer and finally the substrate for the detection enzyme is added. The conversion of the substrate to a visually detectable product is allowed to proceed until optimal visualization of bands and then substrate is washed away. The strip is typically dried, providing a permanent record of the assay result. Bands on the strip indicating antibody reactivity can be compared with control strips to determine the specificity of the immunoreaction. In currently used algorithms for HIV and Lyme testing, a positive test result is defined as the appearance of certain combinations of specific bands.

The Western blot method as described is a multiple step manual procedure, that includes several rate-limiting steps, such as incubating the strips sequentially in the reagent solutions contained in a tray. In typical protocols, incubation with antibody solutions and detection reagents may take 30 minutes to several hours each. Wash steps may take 5–10 minutes each. The total time for processing a blot is not less than one hour, and often several hours. Consequently, the Western blot method is a time-consuming and labor intensive test and therefore disfavored by today's cost conscious health care providers as well as by doctors that are in need of immediate verification of a diagnosis.

However, the Western blot, as well as other membrane-based tests can provide accurate test results for a number of infectious diseases including HIV, Lyme, Babesiosis and Ehrlichiosis. Accurate tests results are needed to treat properly these dangerous diseases, which if untreated can result in serious illness. Moreover, the need to use these more accurate tests is increasing, as Lyme disease is the most rapidly spreading vector-borne disease in the United States, and the HIV positive population is expected to grow from an estimated 20 million people to 30 million people within the next two years.

Accordingly, there is a need for technology that rapidly and efficiently provides accurate test results for infectious diseases.

SUMMARY OF THE INVENTION

In one aspect, the invention provides systems for conducting membrane flow-through assays. The systems can include a filtration procedure which provides for more effective interaction of solutes and membrane-bound ligands. To that end, the systems described herein include a plate that is adapted to receive a cassette which contains a membrane which can contain binding members for binding an analyte of interest in a sample. The systems also include an agitator that agitates fluid applied to the membrane to achieve an even distribution of fluid over the membrane. An even distribution is understood to achieve even and maximal diffusion of fluid into the membrane. The systems further include a pump that is in fluid communication with the cartridge assembly and is capable of generating a pressure differential for drawing the liquid reagent through the membrane. Accordingly, both solvents and solutes can thereby contact molecules bound to the fibers within the thickness of the membrane.

More specifically, the invention is understood to include an apparatus for conducting a membrane flow-through assay. The apparatus can include a plate for carrying a cartridge, or cassette, of the type having a membrane with a binding member for binding an analyte of interest, a base being coupled to the plate for supporting the plate and for allowing the plate to move about at least one axis, an agitator coupled to the plate and capable of moving the plate in a selected motion about the axis, and a pump capable of generating a pressure differential and preferably coupled in fluid communication with the plate for allowing the pressure differential to be applied to the cartridge for drawing a fluid through a membrane of the cartridge, whereby action of the agitator and the pump can allow fluid to distribute evenly across the surface area of the membrane and be drawn through substantially the entire thickness of the membrane.

In one embodiment, the apparatus is adapted such that the plate can removably and replaceably receive the cartridge. This is understood to facilitate the use of disposable cartridge assemblies. The apparatus can be designed for automatic operation and to that end can include a timer, as well as a timer control unit for controlling the duration for which the agitator operates, or for which the vacuum operates. Additionally, the apparatus can include a controlling unit for automatically controlling the operation of the agitator or the vacuum pump. In one embodiment, the control unit includes a programmable memory for allowing a user to select a program of operation for aspirating and agitating a sample material applied to the membrane. The agitator can be, for example, any element suitable for moving the plate and preferably includes a cam assembly for cyclically pivoting the plate above the axis. However, it will be understood that for certain applications other types of agitators can be employed, including ultrasonic transmitters, magnetic devices, blowers or any other system or combination of systems suitable for distributing fluid over a membrane.

In a further embodiment, the apparatus includes a waste container coupled in fluid communication with the pump and being capable of receiving waste fluid diffused through the membrane. In a further embodiment, the apparatus includes a bleed-off valve coupled in fluid communication with the pump. The bleed-off valve can be responsive to the operating condition of the pump, typically whether the pump is on or off, to thereby allow for reducing the pressure differential applied to the cartridge to prevent extended aspiration of fluid through the cartridge after the vacuum has been turned off.

In one embodiment, the plate includes a sealing element for forming a vacuum seal with the cartridge. To this end, the plate can include a compression fitting for forming a substantially fluid tight seal with the cartridge. The plate can provide a perimeter gasket on top of which the cartridge can sit and seal against. When the cartridge sits on top of the gasket, the cartridge and plate together define an interior space. An aperture in the plate can provide access to the interior space and allow a vacuum to be applied within the space. In this way, a vacuum can be applied to the interior space to draw fluid through the fluid-permeable membrane. To this end, the plate aperture can couple to the vacuum pump for allowing the vacuum pump to apply a negative pressure to the interior space.

In another aspect, the invention can be understood as methods for conducting a membrane flow-through assay. Such methods can include the steps of providing a cartridge having a membrane with a binding member for binding an analyte of interest, providing an instrument having a plate for carrying the cartridge, and a base that is moveably coupled to the plate for supporting the plate and for allowing the plate to move about at least one axis. The base can include an agitator that couples to the plate and is capable of moving the plate in a selected motion about the axis, and a vacuum pump that is capable of generating a negative pressure and being coupled in fluid communication to the plate for allowing the negative pressure to be applied to one side of the cartridge membrane. In another step, the cartridge is mounted to the plate, and a fluid sample is applied to the membrane. The agitator is then activated to wash the applied fluid across the surface of the membrane and the vacuum pump is activated for applying a negative pressure to one side of the membrane for aspirating the applied fluid through the membrane, whereby the coordinated action of the agitator and the vacuum pump diffuse the applied fluid through substantially the full thickness of the membrane.

In a further practice, the step of mounting the cartridge to the plate includes a step of sealingly engaging the cartridge to the plate to form a substantially fluid-tight chamber between the chamber and the plate where one wall of the chamber is formed by the membrane, thereby allowing a negative pressure within the chamber to draw fluid through the membrane.

Other aspects and embodiments of the invention will be apparent from the following descriptions of certain illustrated embodiments.

BRIEF DESCRIPTION OF THE FIGURES

The following figures depict certain illustrative embodiments of the invention in which like reference numerals refer to like elements. These depicted embodiments are to be understood as illustrative of the invention and not as limiting in any way.

DETAILED DESCRIPTION OF THE ILLUSTRATED EMBODIMENTS

The invention comprises, inter alia, systems for rapidly processing membrane blot tests, such as Western blot tests for infectious diseases, such as HIV or Lyme disease. Systems according to the invention include a plate that can receive a cartridge that includes the membrane employed in the test. The plate mounts to a base and is capable of pivoting relative to an axis, and is therefore free to rock back and forth about the axis. To that end, the base can include an agitator that will move the plate in a selected motion, such as by rocking the plate back and forth. Additionally, the base can include a vacuum and trap assembly that couples to the plate for allowing a negative pressure to be applied to the one side of the membrane.

The systems described herein can coordinate the action of the agitator and the vacuum assembly to more rapidly conduct the membrane flow-through assay. Specifically, the devices described herein can distribute a fluid sample applied to one surface of the membrane across substantially the full surface area of the membrane, or across a selected portion of the membrane defined by a sidewall seated on top of the membrane. The devices will draw the fluid through substantially the full thickness of the membrane, to maximize interaction between solute molecules and ligands bound to the membrane surface. In one embodiment, the agitator creates a rocking motion that distributes the fluid sample applied to one surface of the membrane across substantially the entire surface of the membrane. The vacuum assembly applies a negative pressure to the opposite side of the membrane to draw the solute molecules through substantially the entire thickness of the membrane. The combined action of the agitator and the vacuum assembly is understood to process membrane blots with bound antibodies, probes and other reagents with increased rapidity compared to conventional methods. Such rapid processing could be applied to Western Blot tests which are currently multi-hour procedures.

Figure 1:
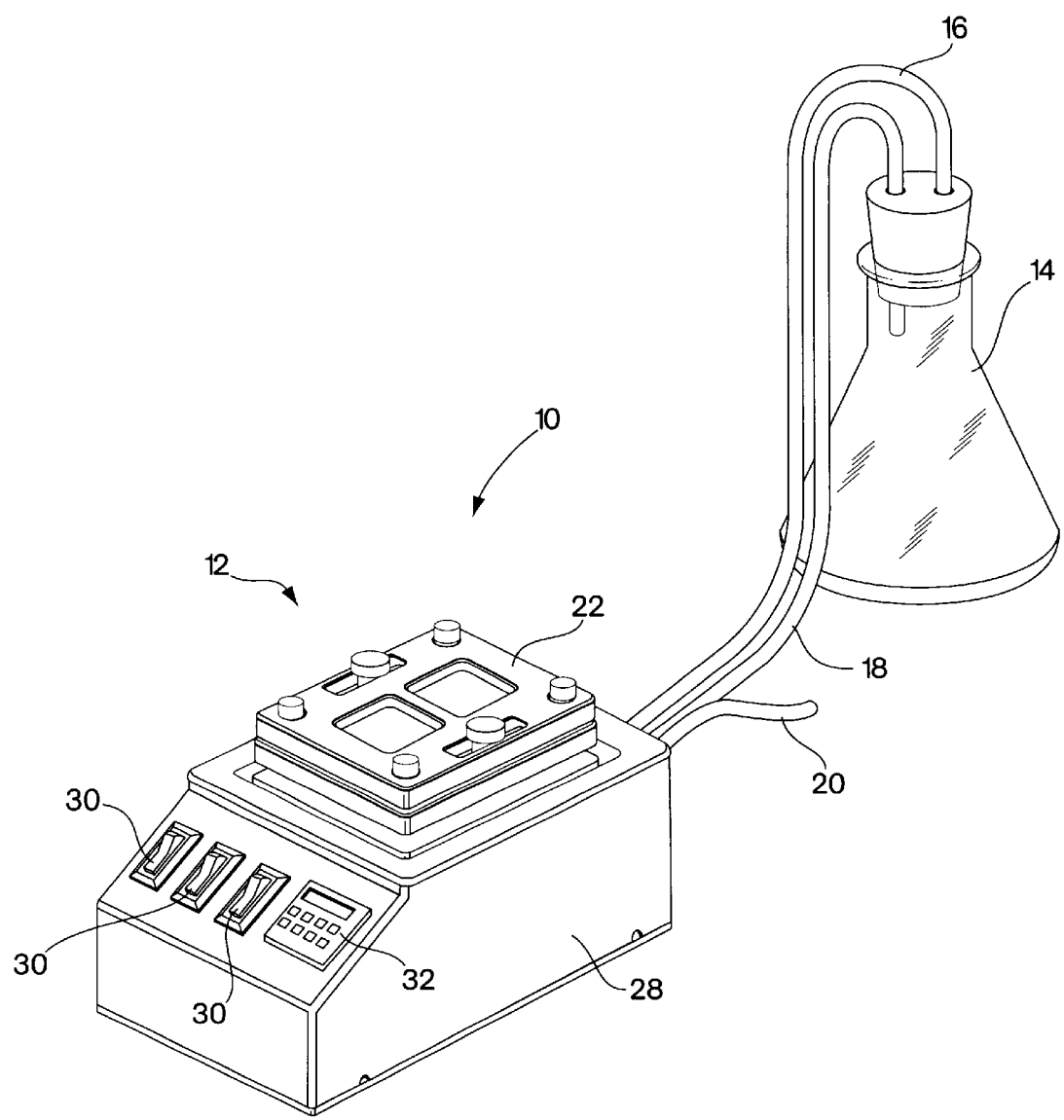
FIG. 1 depicts a system according to the invention for conducting a membrane flow through assay.

FIG. 1 depicts one system according to the invention. The illustrated system 10 includes a processing assembly 12, a waste container 14, a trap input 16, a trap return 18, a stub 20, a plate assembly 22, a housing 28, a plurality of switches 30, and a timer 32.

In general, the system 10 includes a processing assembly 12 that carries a plate assembly 22. The plate assembly 22 can receive a cassette assembly of the type described in U.S. patent application Ser. No. 08/884,017, entitled "Rapid Flow-Through Binding Assay Apparatus and Method", the teachings of which are incorporated herein by reference. This cassette assembly includes a membrane that has ligands bound thereon, A solution can be applied on the surface of the membrane. The processing assembly 12 can agitate the plate assembly 22, such as for example by rocking it back and forth. This agitation is understood to more evenly distribute the fluid material applied to the membrane across the entire surface area of the membrane. As will be described in greater detail hereinafter, the processing assembly 12 can also aspirate the applied fluid through the membrane. The aspirated fluid can be collected within the plate assembly 22 and be vacuum suctioned off and caught within the trap container 14. The waste fluid within the trap container 14 can be disposed of in a sanitary manner.

It is understood that the system 10 performs a membrane flow-through assay in a manner that allows a solution applied to the membrane to be distributed across the surface of the membrane and aspirated through the ligand-containing fibers of the membrane. As it is understood that the rate-limiting step for many membrane assays is the diffusion of solute molecules into and through the membrane, the system 10 depicted in FIG. 1 is understood to more efficiently and rapidly conduct such membrane based assays, as the solute applied to the membrane is evenly distributed across substantially the entire surface of the membrane and by action of the vacuum, drawn through the membrane for more rapid interaction between solute molecules and bound ligands.

Figure 2:
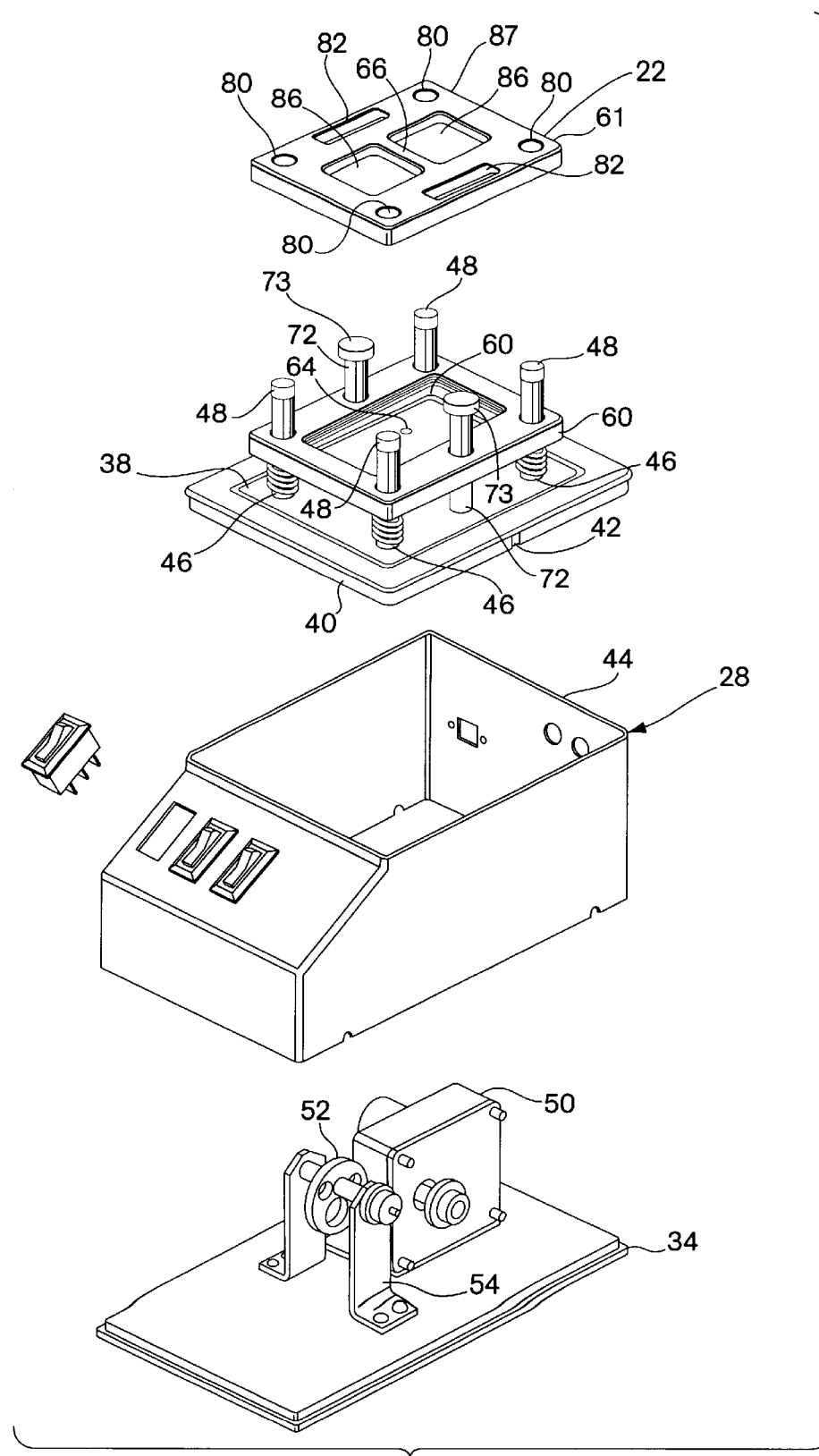
FIG. 2 provides an exploded view of the processing assembly depicted in FIG. 1.

FIG. 2 provides an exploded view of the processing assembly 12 depicted in FIG. 1. As shown in FIG. 2, the processing assembly 12 includes the plate assembly 22, a rocker platform 38, the housing 28 and the agitator assembly 34. Not shown on the agitator assembly 34 depicted in FIG. 2 is the vacuum pump and bleeder valve assembly which, in this embodiment, is also carried within the housing 28. The vacuum pump and bleeder valve assembly will be described in greater detail hereinafter, with reference to FIG. 5.

FIG. 2 shows that the plate assembly 22 can be mounted to the rocker platform 38. Specifically, FIG. 2 shows that the plate assembly 22 can include an upper plate 61 that is removable from a lower plate 60, which is carried on the rocker platform 38. The rocker platform 38 is pivotally mounted to a rim 40 which couples to the rocker platform 38 via pivot points 42, one of such pivot points 42 being shown in FIG. 2. The rocker platform 38 is free to move about the axis defined by the pivot points 42, which are placed on opposite sides of the rim 40. In this way, the rocker platform 38 can pivot about the axis and therefore move relative to the rim 40. The rim 40 is dimensioned to be received by the upper rim 44 of the housing 28. Both the upper and lower plates of the plate assembly 22 can mount through mounting posts 48 to the rocker platform 38. In this way, the plate assembly 22 can be fixed to the rocker platform 38 such that when the rocker platform 38 pivots about the points 42, the plate assembly will be carried through the pivoting motion. The pivoting motion of the rocker platform 38 can be generated by the agitator 34 depicted in FIG. 2. To that end, the agitator 34 includes a motor element 50, which drives an eccentric cam 52 which is mounted on the axle assembly 54. The axle assembly 54 is dimensionally adapted to raise the cam element 52 into contact with the bottom side of the rocker platform 38.

It will be understood that other assemblies can be employed with the invention for allowing the plate assembly to move through a selected path or paths, including assemblies for moving the plate in orbital, lateral, or random paths, as well as paths selected or defined by the user. For such embodiments, the system can include a programmable control unit that can control the agitator for selectively and programmably moving the plate assembly through space. One suitable programmable control unit is a conventional PC-computer system with an input/output card coupled to the system 10, and running a computer program capable of controlling the operation of the agitator being employed to agitate the fluid on the membrane.

The plate assembly 22 can hold a cartridge assembly, such as the type described in the above referenced patent application, which has been incorporated by reference. The membrane in the cartridge can be prepared by any suitable conventional method, such as electrophoretic separation of antigen bands in a polyacrylamide gel followed by transfer of the bands to a membrane. The membrane can then be placed in a cartridge assembly, which comprises an upper, slotted plate and a lower, slotted plate, wherein the slots in the lower plate can act as vacuum aspiration troughs. To that end, the slot pattern of the lower plate can correspond to the slot pattern of the upper plate. The slots of the upper plate extend through the thickness of the plate, so that they are open and accessible along their length. In one embodiment, the slots are approximately 10 cm long×0.35 cm wide. This cartridge assembly, with the membrane, slotted upper plate and apertured lower plate can be placed into the plate assembly 22. The upper plate of the plate assembly 22 closes over the cartridge assembly and compresses the plates of the cartridge assembly together, sandwiching the membrane between the plates. In this way, the slotted upper and lower plates define channels on the membrane, wherein each of the channels are substantially sealed from each other to prevent fluid from one channel spreading to another channel.

Figure 3:
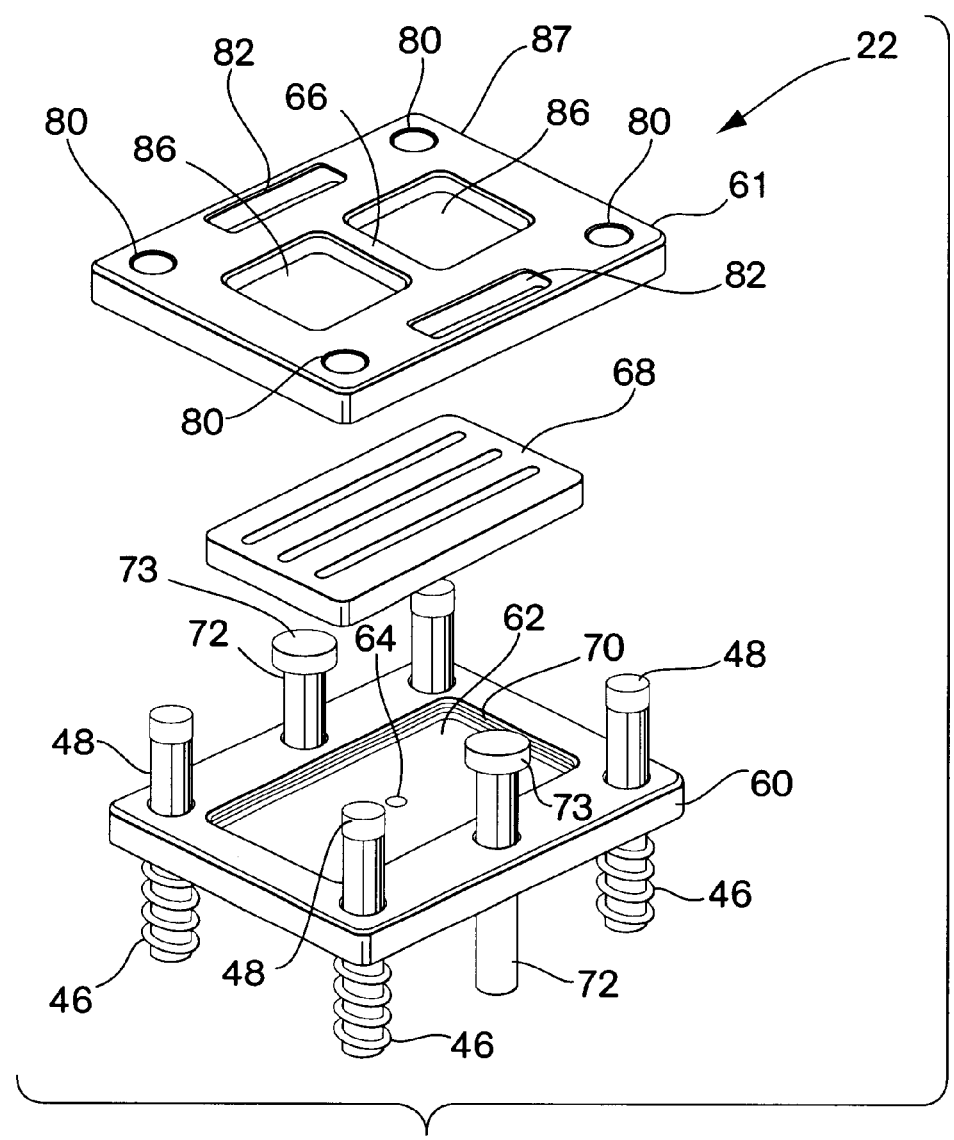
FIG. 3 depicts an exploded view of the plate assembly depicted in FIG. 2.

FIG. 3 provides an exploded view of the plate assembly 22. The depicted lower plate 60 of the plate assembly 22 can have a central pan 62 that serves as the collector for fluid aspirated through the membrane and through the apertures of the lower plate of the cartridge assembly 68. The pan 62 has a central aperture 64 that connects via a length of tubing leading to a trap 14 and from there to the vacuum source. A gasket 70 is disposed around the perimeter of the pan 62 and can support the lower plate of the cartridge assembly 68. In this way, when the cartridge assembly 68 is pressed against the gasket 70, a chamber is defined, wherein one wall is formed by the cartridge assembly 68, and wherein a sidewall is provided with the gasket 70 acting to seal the sidewall against the cartridge assembly 68. The gasket 70 can be formed of a resilient material, such as rubber, or any other material capable of facilitating the formation of a seal. Moreover, elements other than gaskets can be employed, including an outer collar that fits around the perimeter of the cartridge. Once the chamber is formed, a negative pressure within the interior of the chamber will create suction on the backside of the cartridge membrane, and can draw fluid applied to the outside of the membrane, through the membrane and into the chamber.

Returning to FIG. 2, it can be seen that the system 10 includes a clamp-down assembly that comprises the mounting posts 48, the springs 46, the latch assemblies 82 and the latch posts 72. The clamp-down assembly holds together the upper and lower plates of the cassette assembly 68, and holds the cassette assembly 68 tightly between the upper and lower plates of the plate assembly 22. Specifically, the plate assembly 22 has four post holes 80, each of which extend though both the upper and lower plates and each of which will receive a respective one of the mounting posts 48. Each of the depicted mounting posts 48 carries a spring 46 that provides an upward bias, forcing the lower plate 60 upward, away from the rocker platform 38 (This is also shown in FIG. 3). Additionally, the upper plate 61 of plate assembly 22 includes slidable latches 82, each of which can receive a respective one of the latch posts 72, and each of which includes a manually slidable latch that can be slid into engagement with a latch post 72. For example, in one embodiment, each latch post 72 includes a cap 73 at its uppermost end which is dimensioned to allow the forward sliding latch of the latch assembly 82 to slide under and catch against the cap 73. Alternatively, the latch post 72 can include a slot or groove that extends along a length of the latch post and that is dimensioned to receive the forward sliding portion of the latch assembly 82, thus acting as a conventional sliding latch.

The latch and springs cooperate to sandwich together the upper and lower plates of the plate assembly 22. A cartridge assembly 68 seated between the upper and lower plates will be pressed together resulting, as described above, in the membrane of the cartridge assembly being sandwiched between the two plates of the cartridge assembly, to form channels that are sealed separately from each other. These channels can be understood to act as the narrow strips that are processed during a conventional blot assay.

Specifically, when the upper plate 61 of the plate assembly 22 is seated over the mounting posts 48 and the latches 82 are slid forward into engagement with the latch posts 72, the upward bias of the springs 46 provides a mechanical force that holds both plates of the plate assembly 22 tightly in place. In this way, the upper plate 61 of the plate assembly 22 is held down by the latch assembly 82 and the lower plate 60 of the plate assembly 22 is pushed upward against the cartridge assembly 68 by the force of the springs 46. The cartridge assembly 68 is sandwiched between the two plates of the plate assembly 22 and held against the gasket 70 of the lower plate to form a substantially fluid tight seal against the sidewall surrounding the pan 62. In an optional embodiment, the upper plate of the plate assembly 22 has a resilient gasket (not shown) that can sit against the upper plate of the cartridge assembly 68. For example, in the depicted embodiment the upper plate of the plate assembly 22 has two cutouts 86, separated by an arm bar 66. In this embodiment, a figure eight shaped gasket can be seated against the underside of this plate, to sit around the perimeter of the cutouts 86 and across the arm bar 66. This gasket provides the upper plate with a resilient underside which helps compress the cartridge assembly 68 together, and hold the cartridge assembly 68 together as the system 10 agitates and aspirates the cartridge 68.

In an optional embodiment, each of the latch posts 72 has an articulated arm which can be turned to form a right angle relative to the rest of the post 72. The arm can act as a lever for turning the latch post which, in this alternative embodiment, can be screwed down into the rocker platform to compress the plate assembly 22 and sandwich the cartridge assembly therein. The arms can also act as a locking bar for holding the assembly 22 against the rocker platform. Other fasteners can be employed with these plates.

Figure 4:
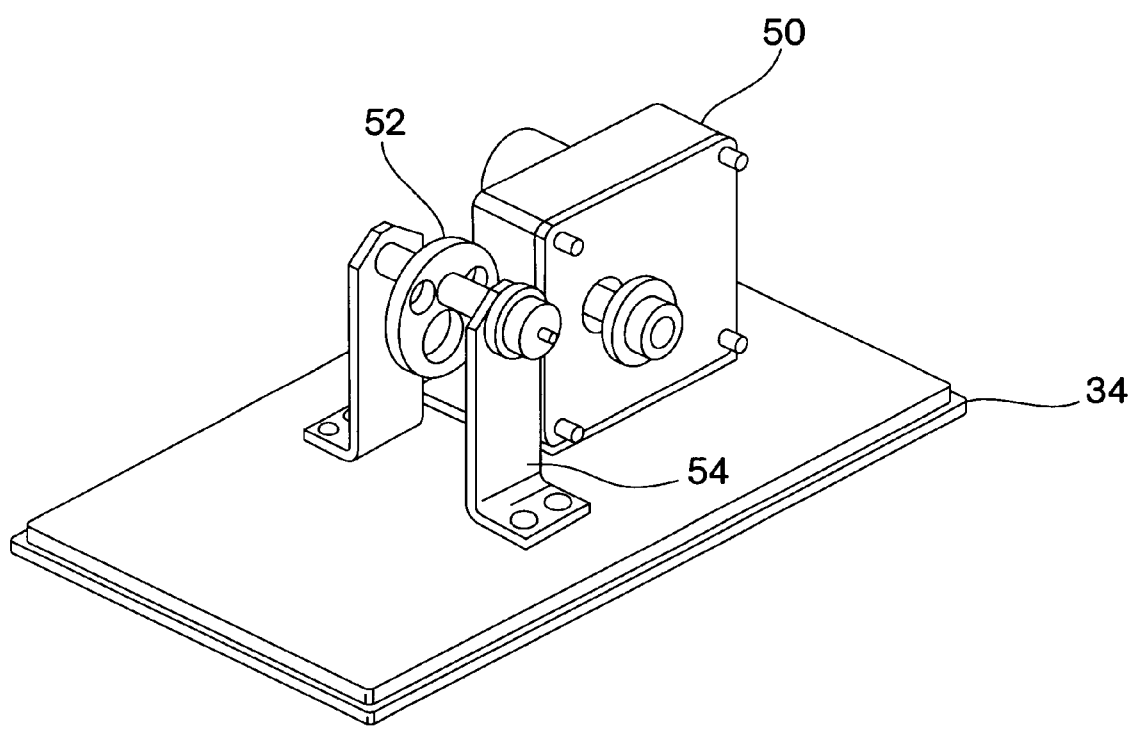
FIG. 4 depicts one embodiment of an agitator suitable for use with the processing assembly depicted in FIG. 1.

FIG. 4 depicts in greater detail one embodiment of an agitator 34 suitable for use with the system 10. The depicted agitator includes a motor 50, an axle and an eccentric cam 52. The cam 52 rotates under the control of the motor 50 and connects by a drive belt to the motor operating at about 60 rpm, which can be a geared motor (such as the type manufactured by Dayton). This speed is not understood as crucial; and both faster and slower speeds are acceptable.

The cam 52 is in contact with the underside of the rocker platform 38 which, as discussed above, is free to pivot about the mounts 42. The cam 52 has an eccentric shape to allow the cam 52 when rotating to push the rocker platform 38 up and down. The design and development of such agitator assemblies is well known in the art of mechanical engineering and any suitable system can be employed with the present invention. In an alternative embodiment of the invention, the plate assembly 22 can couple directly to the agitator. In this embodiment, the agitator can directly move the plate assembly in a selected or random motion. In this embodiment, the agitator can be a hydraulic assembly, a robotic arm, or any other suitable system for moving the plate in a selected motion. Further embodiments of the agitator can include ultrasonic transmitters for moving the fluid by action of ultrasonic energy, magnetic devices which can move magnetic fluid materials, or magnetic components of fluid materials) air blowers for moving fluid by application of air pressure, wiper blades or any other device suitable for distributing fluid over the surface of the membrane.

Figure 5:
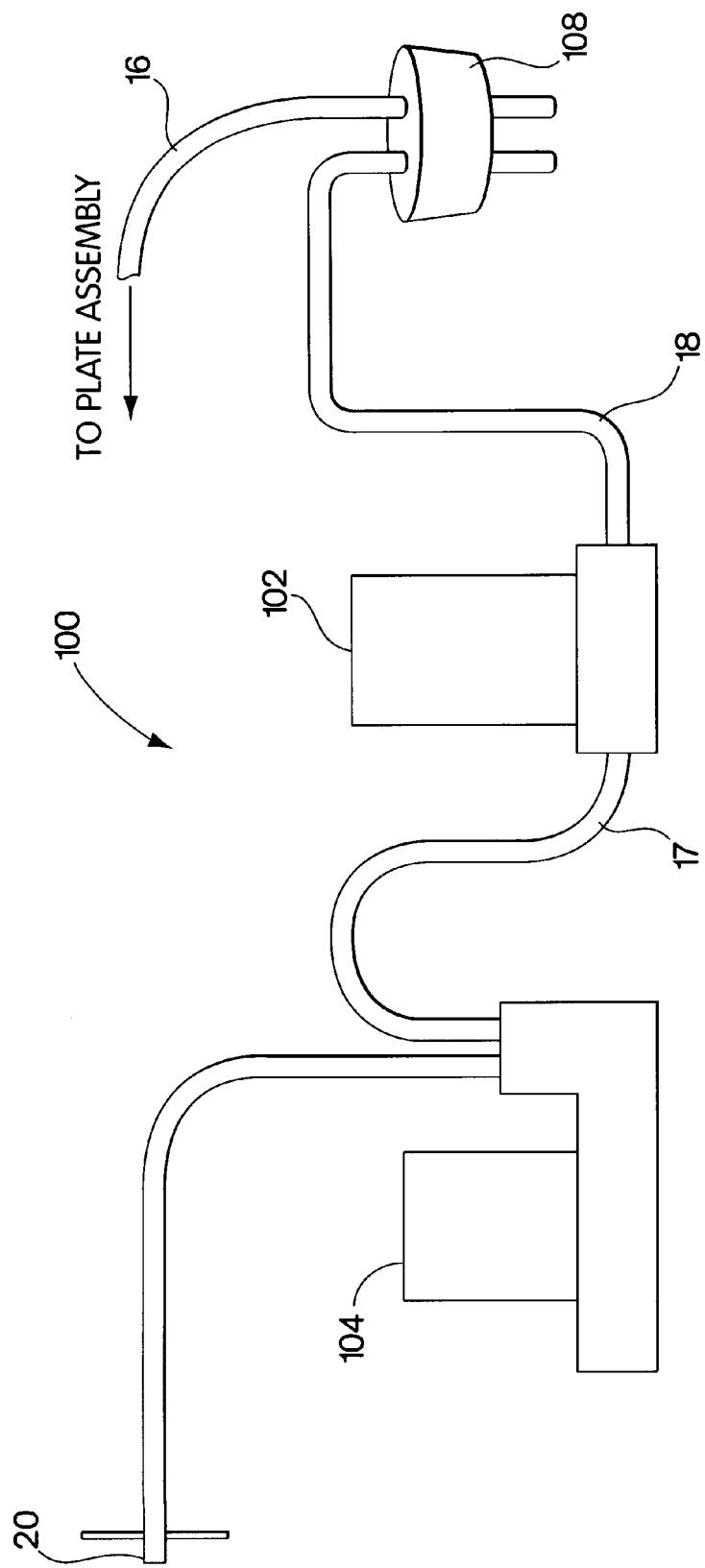
FIG. 5 depicts one embodiment of a vacuum assembly suitable for use with the system of FIG. 1.

FIG. 5 depicts one embodiment of a vacuum pump assembly suitable for use of the present invention for creating a negative pressure which can be applied to one side of a membrane for drawing fluid through that membrane. Specifically, FIG. 5 depicts a vacuum pump assembly 100 that includes a bleeder valve 102 and a pump 104. The bleeder valve 102 and pump 104 are interconnected by a plastic tubing element 17. Also shown in FIG. 5, is the cap 108 of the type that is suitable for being inserted into a flask waste container, such as the waste container 14 depicted in FIG. 1.

The vacuum assembly 100 creates a fluid path created for purposes of creating a vacuum, or a negative pressure, which is understood as a pressure below the pressure of the ambient atmosphere. FIG. 5 depicts that the pump element 104 is coupled through the bleeder valve 102 to the cap 108. When the cap 108 is inserted within a flask, such as the waste container 14 depicted in FIG. 1, the pump 104 acts to extract fluid, typically air, from the flask through the bleeder valve 102. This in turn creates a vacuum within the container 14 which causes fluid to be pulled through the tubing 16. In the system 10 depicted in FIG. 1, the tubing 16 can be coupled to the central aperture 64 of the plate assembly 22, thereby providing a vacuum connection to the plate assembly 22. In operation, the action of the pump 104 creates a negative pressure which is applied by tubing 16 to the plate assembly 22. Fluid from the plate assembly 22 is drawn off through tubing 16 and collected within the waste container 14. The negative pressure is maintained within the container 14 by fluid, typically air, being drawn off by the pump 104 through the fluid path created by the tubing 18, the bleeder valve 102 and the tubing 17. FIG. 5 further depicts that the vacuum pump 104 has an exhaust stub 20 through which air pumped from the flask 14 can be expelled.

The vacuum pump can be any suitable pump, such as a diaphragm-type pump of the type manufactured by KNF Neuberger, Inc., such as model NF10. The pump can provide a working vacuum on the order of 5–10 in. Hg. Other types of vacuum pumps would also be suitable. The assay method can be carried out successfully over a wide range of vacuum pressures, including for example, pressures between about 1–30 in. Hg. Moreover, in alternate embodiments, a negative pressure is developed under the membrane by applying a positive pressure to the opposite side of the membrane. This can be achieved by placing a chamber above the plate assembly, wherein one wall of the chamber can be formed by the plate assembly 22. A positive pressure created within this chamber acts to force fluid through the membrane and can cause fluid to be expelled through a waste vent. Any other system for creating a pressure differential across the membrane for aspirating fluid through the membrane can be practiced.

Both the motor and the vacuum pump operate on 12 VDC. Power can be supplied by an external modular power supply (not shown) such as the Stancor model STA-4812A connected to the 120 VAC house supply, which delivers 12 VDC at 1A max. The power supply is connected to the box via a cord leading to a plug in the rear panel of the box. Thus, the housing contains only 12 VDC components and is exposed only to 12 VDC. This provides for greater safety for the operator when changing tubing within the box or in the event of a liquid spill from the cassette surface into the box. The switches 30 on the base 28 can activate the motor and the vacuum.

Optionally, the control switches 30 can be replaced by an interface to a computer processor, such as a conventional computer workstation, for allowing programmable control over the operation of the system. Alternatively, the system 10 can incorporate a standalone controller unit, such as any of the suitable, commercially available single board computer (SBC) systems commonly employed as controller units for automated or partially automated equipment, such as the SBCs sold by Octagon Systems of Westminster Colo. Such programmable control can include control over the duration for which the agitator operates and duration for which the vacuum is applied. Optionally, the SBC can include a network adaptor for connecting to a computer network for receiving instructions or for allowing for remote control of the process. These control systems can operate under the control of a computer program that provides a user interface for allowing programmable control over the elements of the system. The computer program can be written in any suitable langauge including the C programming language. Moreover, the system can include sensors for monitoring certain characteristics of the process, such as the pressure differential across the membrane, the temperature of the membrane, the rate at which the cartridge assembly is being agitated, the movement of the cartridge assembly, or any other characteristic of the process. This allows the system to employ a feedback control system for controlling the conditions of the process, by monitoring the characteristics of the process as the assay is being performed. Such feedback systems are well known in the art of electrical engineering and are described in F. G. Shinskey, *Process Control Systems, Application, Design and Tuning*, McGraw-Hill (1988).

In operation, a technician can mount a disposable cartridge assembly 68 within the plate assembly 22 and start applying test solutions to the channels defined by the slot pattern of cartridge assembly 68. For a given test (e.g., Lyme or HIV) the operator will remove a cassette from its package and wet it in a tray of distilled water. The cassette 68 will be mounted in the device, between upper and lower holding plates of assembly 22, which can be machined from aluminum and be quite rigid. Pressure is applied by pushing down on the upper plate, which compresses four springs 46 below the corners of the lower plate. The pressure is maintained by sliding two latches 82, one on either side of the assembly 22 into a position which locks them against the flanges of latch posts 72. Sufficient pressure is produced in this way to seal cassette channels against the membrane so as to prevent cross-channel leakage.

Once the cassette is mounted, the operator can add approximately 500 microliters of diluted serum sample (at 25×dilution) into each channel. Not all channels need be used. The same volume per channel of al reagents is used. The agitator is turned on and can be left on for all subsequent steps. However, the operator can stop the agitation for reagent additions if desired. The cassette can be incubated for 4 minutes, after which the vacuum is turned on and the samples aspirated completely through the membrane. Wash solution (typically buffered saline with some detergent, e.g. PBS/0.05% Tween-20) is added and aspirated twice. Diluted enzyme conjugate (e.g., goat anti-human IgG-alkaline phosphatase) is added and incubated for 4 minutes. The same wash steps are repeated, with a final wash with distilled water. Enzyme substrate (e.g., BCIP/NBT, 5-bromo-4-chloro-3-indolyl phosphate/nitroblue tetazolium) is added and incubated for 4 minutes, then aspirated. A final wash with distilled water completes the test. The rocker and vacuum are then turned off and the cassette removed. The cassette is opened and the membrane is removed for evaluation. Colored bands indicate sites of antibody attachment and can be used to analyze test results according to algorithms specific for the disease tested. The entire process can be completed in approximately 15–20 minutes. Application of test solutions could be performed manually, or by a robotic liquid handling system under software control. In all cases, a visual or otherwise detectable pattern of reactivity, in the form of bands or otherwise, is generated in each test channel, and can be analyzed to obtain a test result.

In the above description, the technician operates the device through the switches 30 which activate the agitator and the pump assembly. The timer depicted in FIG. 1 can act as a conventional timer or a countdown timer, and is employed by the technician for monitoring the duration for which the pump or the agitator operates. In the alternate embodiment, the device can couple to a computer, such as a PC compatible-computer, for allowing automated control, and programmable control of the agitator and the pump.

Figure 6:
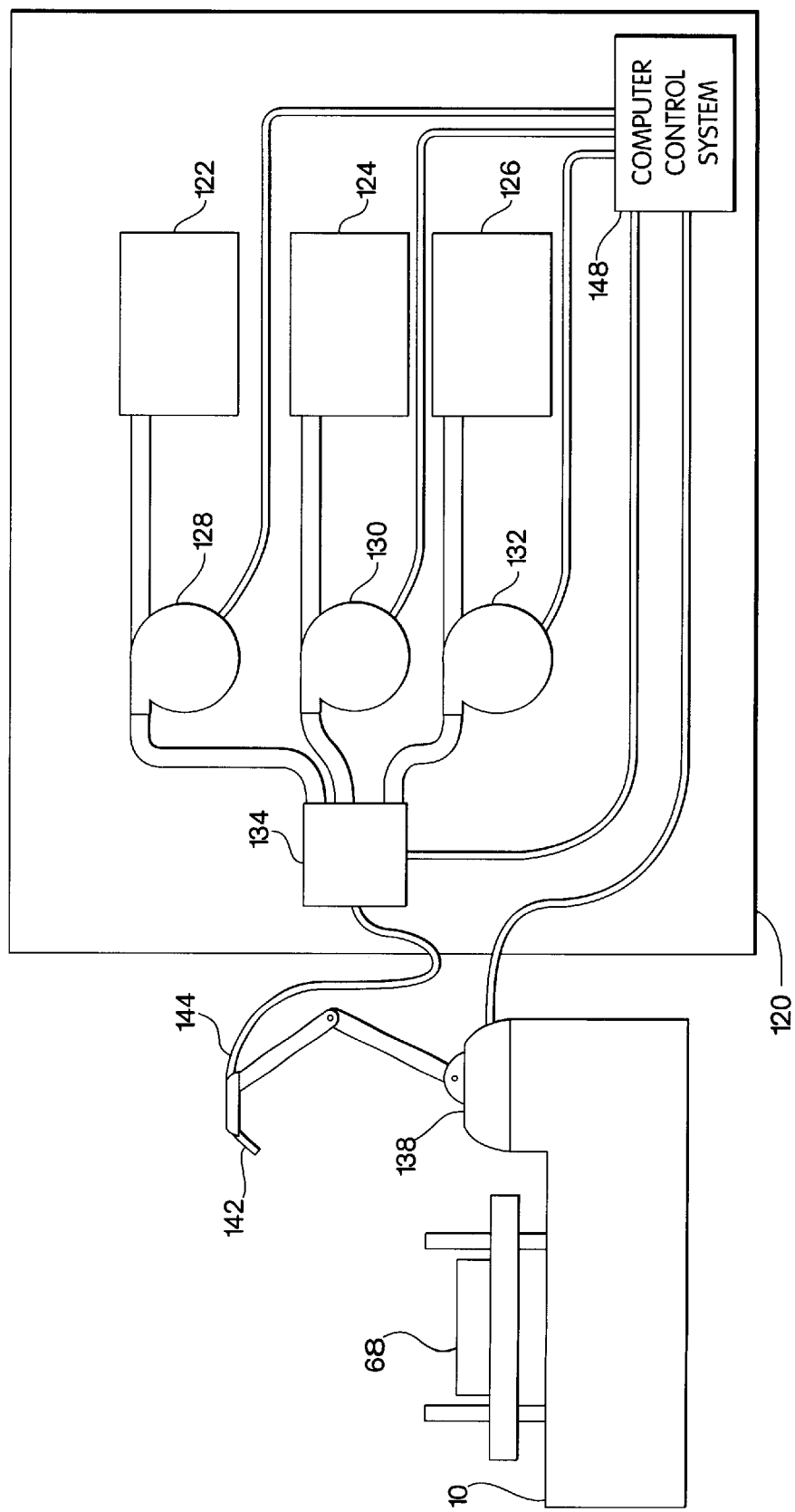
FIG. 6 depicts an automated fluid dispensing system for use with the system of FIG. 1.

FIG. 6 depicts a alternative embodiment of the invention which includes an automated liquid handling system. The automated liquid handling system depicted in FIG. 6 comprises two components, a robotic arm assembly 138 with a liquid dispensing end effector 142 and a computer-controlled metering pump assembly 120. The metering pump assembly 120 is shown in functional block diagram form, however, it will be understood that the metering pump assembly 120 can be designed as a pump assembly which fits within the housing of the system 10 which also carries the agitator and pump assembly for aspirating fluid through the membrane of the cassette assembly 68.

The metering pump assembly 120 depicted in FIG. 6 includes a computer-controlled system 148, reservoirs 122, 124 and 126, metering pumps 128, 130 and 132 and an optional valve 134. The depicted computer control system 148 is connected to each of the metering pumps 128, 130 and 132 for controlling the operation of the metering pumps. In the depicted embodiment, the computer control assembly 148 also couples to the valve 134, for opening the valve to allow fluid from one of the three metering pumps to reach the end effector 142 of the robotic arm assembly 138. In an alternate embodiment, no valve is included, and fluid is directed to the end effector by action of one of the metering pumps.

The computer control system 148 can be a single board computer which can independently operate the metering pumps and valve or can also be configured to operate under the other elements of the system 10 including the agitator and pump assembly for aspirating fluid through the membrane.

The reservoirs 122, 124 and 126 can be any suitable fluid container for storing reagents and wash buffer. Each of the reservoirs can be small vials capable of holding 10 to 50 ml. of fluid. The vials can be stored within the housing of the system 10, or in an alternative embodiment, the reservoirs can be larger fluid containers that are stored outside of the housing of the system 10. Each of the reservoirs 122 through 126 connects to a respective one of the metering pumps 128 to 132. In this way, the reservoirs provide fluid to each of the metering pumps for being dispensed through the end effector 142 of the robot 138 and into one or more of the channels within the cassette 68. Typically, each of the metering pumps operate to draw fluid from its respective reservoir, and pump the fluid through the valve 134 into the end effector 142 of the robotic arm 138. The valve 134 is an optional component that can act as a back flow valve which prevents fluid within the end effector from flowing back to the metering pumps when the metering pumps are inactive.

FIG. 6 further depicts the robotic arm assembly 138 which includes the end effector 142 which couples by tubing 144 to the optional valve 134. The depicted end effector 142 is a needle-like tubular element that has a nozzle in its distal end for allowing fluid pumped through tubing 144 to be ejected from the end effector 142. The robotic arm assembly can be a conventional robotic arm assembly which can be manipulated under the control of the computer control system 148 for positioning the end effector 142 above or into the channels of the cassette assembly 168. In this way, the computer control system 148 can manipulate the robotic arm assembly 138 to apply liquid reagents to the membrane of the cassette assembly 168. In one practice, the robotic assembly 138 can dispense a metered amount of reagent into each channel of the cassette assembly 68. In an alternative embodiment, the end effector 142 can have a plurality of nozzles, each being spaces from each other the same distance as the channels are spaced apart, to thereby allow the parallel dispensing of metered amounts of reagent into each channel of the cassette assembly 68. The computer control system 148 can cycle the dispensing of liquid reagent onto the membrane such that the reagents are sequentially dispensed from each of the reservoirs 122, 124 and 126. In one practice, reservoir 122 contains an enzyme conjugate, the reservoir 124 contains an enzyme substrate and the reservoir 126 contains a wash buffer. In operation, the computer control system 148 can operate the pump assemblies 128 through 132 and the robotic arm assembly 138 to dispense enzyme conjugate into the channels of the cassette 68, then send wash buffer through the tubing of the system and through the end effector 142, and then dispense enzyme substrate through the end effector 142 and into the channels of the cassette assembly 68.

In an alternate embodiment of the invention, the end effector 142 can also be equipped with an ultrasonic transmitter that can be inserted into the channels of the cassette assembly 68 for directing ultrasonic energy onto the liquid applied to the membrane. This is understood to provide an alternative way for agitating the fluid applied to the membrane, to thereby distribute the fluid across the surface of the membrane. In a further alternative embodiment, the end effector 142 can contain a plurality of ultrasonic transmitters each of which can be inserted by the robotic assembly 138 into a respective one of the channels of the cassette assembly 68 for using the ultrasonic energy from the transmitters to dispense, in parallel, fluid applied to the membrane of the cassette assembly 68.

Many aspects of the device can be varied without departing from the basic principles of design and use; i.e., cassettes with varying numbers of channels and varying geometries of channels, including a series of circles, different methods for rocking and aspirating and timing.

With respect to collection of aspirated fluid, generated during the above described procedure, the liquid waste path in the system 10 starts at the bottom of the plate assembly 22. Liquids flowing through the membrane in the cassette assembly 68 are collected in the base of the holding plate and exit through the hole 64 in the center of this plate. Plastic tubing 16 connected to this hole via a threaded adaptor runs through the housing and out to the external vacuum trap 14. The depicted trap is a 500 ml flask with entry and exit openings in the cap 108. A second plastic tube 18 runs from the trap 14 into the housing, where it is connected to an electronic bleeder valve 102. The bleeder valve 102 is connected via tubing 17 to the vacuum pump 104. The output end of the vacuum pump 104 is connected to the stub 20.

The function of the bleeder valve 102 is to dissipate the vacuum instantly when the vacuum pump 104 is turned off. The bleeder valve 102 is therefore electrically connected to the vacuum pump 104, so that the switch 30, which turns the vacuum pump 104 off, simultaneously turns the bleeder valve 102 on. This operation prevents the continuous aspiration of liquid through the cassette which would otherwise occur due to vacuum retained within the system. In an alternative embodiment the entire cartridge can be a fluid tight assembly that sits on the rocker platform and joins directly to a vacuum hose. In this way the negative pressure can be applied to a chamber within the cartridge assembly for drawing the fluid through the membrane, and fluid drawn through the membrane can be suctioned off through the vacuum system and disposed of as necessary.

The systems and methods described above can be carried out with a cartridge device which is described in U.S. patent application Ser. No. 08/884,017, that has been incorporated by reference. However, it will be apparent that any suitable membrane assembly can be employed with the present invention, and the invention is not to be limited to the cartridge assemblies referenced. Assay performance is improved as the cassette is agitated, typically by rocking, to distribute liquid reagents evenly over the surface of the membrane during incubation and wash steps. Even distribution of liquid over the membrane ensures that solutes, including antibodies and enzyme-antibody conjugates, diffuse evenly and maximally into the membrane where they come into contact with membrane-bound antigens and antigenantibody complexes, respectively. To provide for maximal interaction between liquid reagents and the membrane, each liquid reagent applied during the test procedure is aspirated through the membrane by vacuum. Both solvents and solutes thereby contact molecules bound to the fibers of the membrane within its thickness. Membranes used in solid phase binding assays vary in thickness, but a typical nitrocellulose membrane is 0.005" thick. Such membranes are composed of interwoven fibers forming a three-dimensional matrix, to which antigens bind by a combination of hydrophilic and hydrophobic interactions. Given the proportion of surface area to volume of the membrane, it is understood that most of the molecules whose detection is intended by a given assay will be bound within the interior space of the membrane. This rapid filtration procedure can be applied to a variety of membrane-based diagnostic tests, including Lyme, and HIV, and the systems described herein are not to be limited to any particular application.

It will be understood that the embodiments of the invention which have been described are illustrative of some of the applications and principles of the present invention. Various modifications may be made by those skilled in the art without departing from the spirit and scope of the invention. For example, the systems described herein can be modified to include robotic handling systems for applying the reagents to the membrane surface. Similarly, the systems can be modified to include heat lamps, cooling devices, or any other equipment which may be necessary or beneficial for a particular membrane-based test. Moreover, it will be understood that the systems of the invention provide, inter alia, rapid filtration procedures that can be applied to a variety of membrane-based tests. Accordingly, the invention is not to limited to the above shown illustrated embodiments, but is to be understood by the claims set forth below, which are to be interpreted as broadly as allowed by law.

I claim:

1. An apparatus for conducting a membrane flow-through assay, comprising:
   a plate for carrying a cartridge having a membrane with a binding member for binding an analyte of interest,
   a base being movably coupled to the plate for supporting the plate and for allowing the plate to move about at least one axis,
   an agitator coupled to the plate and being positioned within the base for moving the plate in a selected motion about the axis, and
   a vacuum pump capable of generating a negative pressure and being positioned within the base in fluid communication to the plate for allowing the negative pressure to be applied to a cartridge for drawing a fluid sample through a membrane of the cartridge,
   whereby action of the agitator and the vacuum pump can allow a fluid to diffuse through substantially the entire membrane.

2. An apparatus according to claim 1, wherein the plate removably and replaceably receives the cartridge to facilitate the use of disposable cartridge assemblies.

3. An apparatus according to claim 1, further comprising a timer.

4. An apparatus according to claim 1, further comprising a timer control unit for controlling the duration for which the agitator operates.

5. An apparatus according to claim 1, further comprising a control unit for automatically controlling the operation of the agitator and vacuum pump.

6. An apparatus according to claim 4, wherein the control unit includes a programmable memory for allowing a user to select a program of operation for aspirating and agitating a sample material applied to the membrane.

7. An apparatus according to claim 1, wherein the agitator includes a cam assembly for cyclically pivoting about the axis.

8. An apparatus according to claim 1, wherein the agitator includes an ultrasonic transmitter.

9. An apparatus according to claim 1, further comprising a waste container coupled in fluid communication with the vacuum pump for receiving waste fluid diffused through the membrane.

10. An apparatus according to claim 1, further comprising a bleed-off valve coupled in fluid communication with the vacuum for reducing the negative pressure applied to the cartridge to thereby prevent extended aspiration of liquid through the cartridge.

11. An apparatus according to claim 1, wherein the plate includes a sealing element for forming a vacuum seal with the cartridge.

12. An apparatus according to claim 1, wherein the plate includes a compression fitting for compressing a membrane held within the cartridge.

13. An apparatus according to claim 1, further including a control panel having an activation control for the agitator and an activation control for the vacuum pump, to thereby allow a user to control independently the agitation and aspiration of reactant fluid being applied to the membrane.

14. An apparatus according to claim 1, further including a cooling unit for controlling the temperature of the membrane.

15. An apparatus according to claim 1, further including a heating unit for raising the temperature of the membrane.

16. An apparatus for conducting a membrane flow-through assay, comprising
   a plate assembly for carrying a cartridge having a membrane carried therein,
   a base being coupled to the plate assembly for supporting the plate assembly,
   an agitator being positioned within the base and capable of distributing a fluid material over the surface of the membrane, and
   a pump assembly being positioned within the base and capable of generating a pressure differential and being coupled in fluid communication to the membrane for applying the negative pressure to a side of the membrane for drawing a fluid through the membrane, whereby action of the agitator and the pump assembly can allow a fluid to diffuse through substantially the entire membrane.

17. An apparatus according to claim 16, wherein the agitator includes an ultrasonic transmitter.

18. An apparatus for conducting a membrane flow-through assay, comprising
   a plate assembly for moving about at least one axis while positioned on the apparatus, the plate assembly carrying a cartridge having a fiber membrane carried therein wherein said membrane includes a binding element held with the fiber of the membrane, and
   a pump assembly capable of generating a pressure differential across the membrane for drawing a fluid through the membrane, whereby action of the pump assembly can allow a fluid to diffuse through substantially the entire membrane.

19. An apparatus according to claim 18, wherein the cartridge assembly includes an upper plate and a lower plate each of which has a slot pattern defined therein to provide channels for passing fluid through the cartridge assembly and through the fiber membrane, and
   wherein the pump assembly is in fluid communication to each channel of the fiber membrane, whereby fluid is drawn through each separate channel to thereby diffuse fluid through separate portions of the fiber membrane.

* * * * *